US006847845B2

(12) United States Patent
Belden

(10) Patent No.: US 6,847,845 B2
(45) Date of Patent: Jan. 25, 2005

(54) CONNECTION SYSTEM FOR A MULTI-POLAR LEAD

(75) Inventor: Elisabeth L. Belden, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 459 days.

(21) Appl. No.: 10/034,143

(22) Filed: Dec. 28, 2001

(65) Prior Publication Data

US 2003/0125780 A1 Jul. 3, 2003

(51) Int. Cl.[7] ............................................... A61N 1/365
(52) U.S. Cl. ...................................................... 607/37
(58) Field of Search ............................ 607/4, 5, 9, 27, 607/36, 37, 38, 119, 122–127

(56) References Cited

U.S. PATENT DOCUMENTS

| | | | |
|---|---|---|---|
| 4,161,952 A | | 7/1979 | Kinney et al. .............. 128/786 |
| 4,506,680 A | | 3/1985 | Stokes ........................ 128/786 |
| 4,577,642 A | | 3/1986 | Stokes ........................ 128/784 |
| 4,606,118 A | | 8/1986 | Cannon et al. ............... 29/825 |
| 4,628,934 A | * | 12/1986 | Pohndorf et al. ............ 607/27 |
| 4,679,318 A | | 7/1987 | Bright .......................... 79/840 |
| 5,374,279 A | | 12/1994 | Duffin, Jr. et al. |
| 5,387,233 A | | 2/1995 | Alferness et al. ........... 607/126 |
| 5,662,692 A | * | 9/1997 | Paspa et al. .................. 607/37 |
| 5,906,634 A | * | 5/1999 | Flynn et al. .................. 607/37 |
| 5,957,970 A | | 9/1999 | Shoberg et al. ............. 607/722 |
| 5,964,795 A | | 10/1999 | McVenes et al. ........... 607/122 |
| 6,006,122 A | | 12/1999 | Smits .......................... 600/373 |
| 6,192,280 B1 | | 2/2001 | Sommer et al. ............. 607/122 |
| 6,295,475 B1 | | 9/2001 | Morgan |

OTHER PUBLICATIONS

LeClercq et al., "Acute Hemodynamic Effects of Biventricular DDD Pacing in Patients with End–Stage Heart Failure," Dec. 1998, J Am Coll Cardiol 1998;32:1825–31.
Cazeau et al., "Four Chamber Pacing in Dilated Cardiomyopathy," Nov. 1994, PACE 1994; 17 (Pt. II):1974–1979.

* cited by examiner

*Primary Examiner*—George Manuel
(74) *Attorney, Agent, or Firm*—Michael C. Soldner; Girma Wolde-Michael

(57) ABSTRACT

A connection system for electrically coupling selected conductors carried by a medical electrical lead to a source of energy such as an implantable pulse generator is disclosed. The connection system includes a first port that may be coupled to at least two conductors carried by a lead. The first port electrically couples the at least two conductors to each other, and to the source of energy. A second port is provided to respectively electrically couple at least one additional lead conductor to the source of energy.

22 Claims, 7 Drawing Sheets

CONNECTION SYSTEM FOR A MULTI-POLAR LEAD

RELATED APPLICATIONS

This Application is related to commonly-assigned patent application Ser. No. 10/034,905, filed on even date herewith, entitled "improved system for Providing Electrical Stimulation to a Left Chamber of a Heart".

FIELD OF THE INVENTION

The present invention relates generally to a configurable connection system for a medical electrical lead; and more specifically, relates to an improved connector for a multi-polar lead.

BACKGROUND OF THE INVENTION

It has long been known that implantable medical electrical leads may be positioned transvenously within one or more chambers of the heart or the associated vascular system to provide electrical stimulation to cardiac tissue. Often, such a lead includes multiple electrodes. For example, a lead may include a pair of pace/sense electrodes. This electrode pair may be used to deliver low-voltage stimulation such as pacing pulses to the tissue. Often, the electrode pair will include a tip electrode that is used as the cathode to supply such pacing pulses. In the case of electrodes positioned within the cardiac vasculature, this is not necessarily the case, however. That is, when electrodes are positioned within a vein, the most distally-positioned electrode is not necessarily the best electrode choice for use as the cathode. In this type of situation, threshold testing may be performed to determine which electrode of an electrode pair will provide better capture of the heart, and is therefore more suitable for use as the cathode.

As another example, some leads include one or more pace/sense electrodes to provide pacing and sensing capabilities, and at least one additional high-voltage electrode to provide high-voltage therapy, including cardioversion/defibrillation shocks. In some instances, it is advantageous to electrically couple the high-voltage electrode with at least one of the pace/sense electrodes prior to high-voltage therapy delivery, since this increases the amount of tissue affected by the therapy. In other words, it increases the "shadow area" of the high-voltage electrode. Preferably, one or more pace/sense electrodes being uses as an anode during pacing therapy is selected for electrically coupling to the high-voltage electrode.

In either of the above-described examples, it is necessary to selectively couple an electrode to circuitry within an implantable pulse generator or another signal generator. This electrical coupling is generally performed after threshold testing or another type of electrical signal testing is performed. However, current lead systems do not provide a mechanism for readily these types of selective connections. Therefore, what is needed is an improved connection system for a multi-polar lead that will solve at least some of the foregoing problems.

SUMMARY OF THE INVENTION

The current invention provides a connection system for coupling selected conductors carried by a medical electrical lead to a source of energy such as an implantable pulse generator. The connection system includes a first port that may be coupled to at least two conductors carried by a lead. The first port electrically couples the at least two conductors to each other, and to the source of energy. A second port is provided to respectively electrically couple at least one additional lead conductor to the source of energy.

According to one exemplary use of the current connection system, the system provides a means for selectively coupling a high-voltage coil electrode of a medical lead to a second electrode carried by the lead to increase the shadow area of the coil electrode during high-voltage therapy. As another example, the connection system allows for cathode selection between multiple pace/sense electrodes provided on a lead body.

According to another aspect of the invention, a connection system for use in electrically coupling a source of energy to a multi-polar medical electrical lead having at least three conductors is disclosed. The connection system includes a first port to selectably electrically couple to at least two of the at least three conductors, and a second port to electrically couple to another one of the at least three conductors. The connection system also includes a connector to couple to the source of energy, where the connector may include an industry standard connector such as an IS-1 or DF-1 connector, or may include a non-standard connector.

In another embodiment, a medical system to provide electrical stimulation to living tissue is disclosed. The system includes a lead having at least three conductors, each of the conductors being coupled to a respective electrode. The system further includes an energy source, and a connection system to electrically couple ones of the at least three conductors to the energy source. The connection system includes a first port to electrically couple at least two selected ones of the at least three conductors together in common, and second port to electrically couple to at least one other one of the at least three conductors. The connection system further includes a connector to respectively electrically couple the first and second ports to the energy source.

Other scopes and aspects of the current invention will become apparent to those skilled in the art from the following description and the accompanying drawings.

BRIEF DESCRIPTION OF THE DRAWINGS

FIG. 10A is an end view of another embodiment of mating interface of

FIG. 4.

FIG. 10C is an end view of another embodiment of the mating interface of FIG. 4 as may be used with the connector of FIG. 10B

DESCRIPTION OF THE INVENTION

The present invention provides a connection system for a multi-polar lead. Although a single embodiment of the lead is provided herein for exemplary purposes, it will be understood that any multi-polar lead having electrodes adapted to be selectively configured may usefully employ the current connection system. The lead disclosed herein is therefore solely provided for illustrative purposes.

Figure 1:
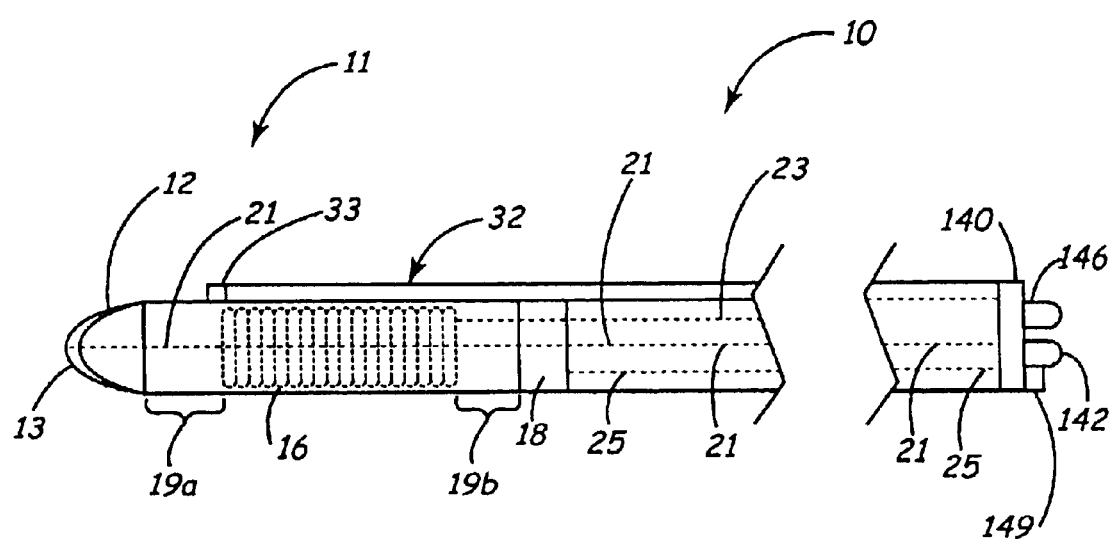
FIG. 1 is a side view of one embodiment of a lead system as may employ the current invention.

A. An Exemplary Lead System as may be Adapted for Use with the Current Invention FIG. 1 is a plan view of one embodiment of a lead system as may be adapted for use with the current invention. The lead includes an elongated body 10 that may be of any conventional lead construction known in the art. For example, the exterior of lead may be formed of silicone, polyurethane, or a non-porous or dense PTFE.

The distal end of the elongated body includes a tip electrode 12 for pacing and sensing in the left ventricle. This electrode could be any of the various types of pacing electrodes known in the art such as a porous platinized electrode assembly. A tip electrode is shown, although a ring electrode located proximate the distal end of the elongate body 10 could be used in the alternative. In one embodiment, this electrode is a steroid-eluting porous pacing electrode, as described in commonly-assigned U.S. Pat. Nos. 4,506,680, 4,577,642; 4,606,118 incorporated herein by reference. The electrode may be constructed of porous, sintered platinum, titanium, or a similar bio-compatible metal.

Tip electrode 12 could include means to aid in fixing the electrode assembly at a desired site of implant within the branch vein. For example, the electrode could include flexible tine-like or fin structures. Fixation devices of this nature are disclosed in U.S. Pat. Nos. 5,964,795, 6,006,122, and 5,387,233 which are incorporated herein by reference. Alternatively, the lead body 10 could be shaped to have side-to-side undulations to wedge the lead within the vessel and aid in retaining the lead body at the implant site.

Shocking electrode 16, located proximal to tip electrode 12 provides cardioversion/defibrillation stimulation, and, in one embodiment, may be used as an anode for bipolar pace/sense therapy in conjunction with the pace/sense cathode, as will be discussed further below. Shocking electrode 16 is a coiled electrode that may be of any construction known in the art. In one embodiment, the coil is isodiametric with respect to the lead body. Such isodiametric electrode coils may be molded into the electrode body or the coils may be machined to provide a flush surface. This is described in U.S. Pat. No. 4,161,952, issued to Kinney et al. Similarly, U.S. Pat. No. 5,957,970 to Shoberg discloses an isodiametric defibrillation lead as may be used with the current invention. The lead described in the '970 patent is manufactured by removing a portion of an extruded tubular lead body in the region of the coil so that the electrode is flush with the surface of the lead.

Figure 2:
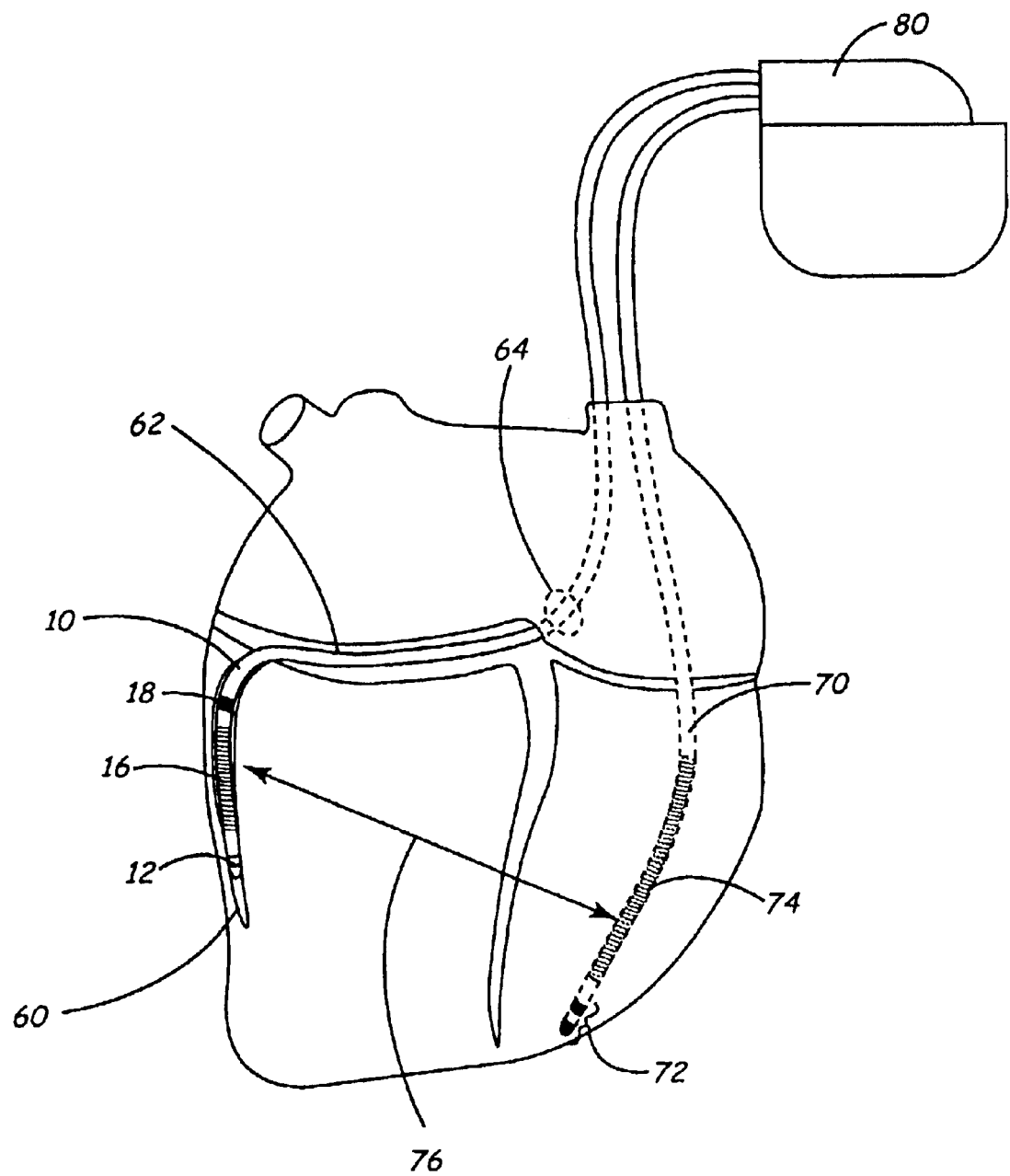
FIG. 2 is a posterior view of the heart illustrating the lead system of FIG. 1 implanted within a branch vein of the coronary sinus.

Shocking electrode 16 may be encased in a layer of porous PTFE material or expandable PTFE (ePTFE), as shown in FIG. 2. The porous PTFE jacket 30 is designed to prevent tissue in-growth around the coils of the shocking electrode. Shocking electrode 16 is electrically coupled to a conductor 23 (shown dashed) extending to a connector 140 at the proximal end of the lead. More specifically, conductor 23 is electrically coupled to a connection member shown as pin 146 of the connector.

In one preferred embodiment of the current invention, elongate body 10 may further include a ring electrode 18. In FIG. 1, this electrode is shown located just proximal to the shocking electrode 16, although it may be positioned distal to the shocking electrode 16 in another embodiment. Pacing pulses may be delivered between tip electrode 12 and ring electrode 18. Additionally, ring electrode 18 may be used as the pace/sense cathode if the location of ring electrode is more favorable for such therapy than the most distal electrode. If the ring electrode 18 is selected as the pace/sense cathode, tip electrode 12 may be electrically coupled in common with the shocking electrode 16 to augment the shadow area of the shocking electrode. Similarly, if the most distal electrode 12 is selected to be the pace/sense cathode, the ring electrode 18 may be electrically coupled with the shocking electrode 16.

In the illustrated embodiment, conductor 21 extends to a connection member shown as pin connector 142. Conductor 25 extends to a similar pin that is not shown in FIG. 1.

As noted above, the construction of the lead body may be of any type known in the art. Conductors 21, 23, and 25 may be of a cable or coil design, and may reside within individual lumens formed in the insulation. In another embodiment, one or more of the conductors may be coils positioned coaxially with respect to each other, with insulation provided between adjacent coils.

The lead body may further include a lumen for receiving a stylet For example, one of the conductors 21, 23 and 25 may be coiled to define such a lumen, or the lumen may be formed within the insulation. In yet another embodiment, the lumen may extend through the distal end of elongate body 10 and tip electrode 12. In this instance, a guidewire may be advanced beyond the lead distal tip for positioning the lead body within the coronary sinus or a branch vessel. In this embodiment, a tip seal 13 may be provided at the distal end of the lumen, as described in commonly-assigned U.S. Pat. No. 6,192,280 incorporated herein by reference. This tip seal prevents the ingress of bodily fluids into the lumen.

The lead body 10 of FIG. 1 is further shown having a side lumen 32 offset from the surface of the lead body. This side lumen may extend from the proximal lead end to any desired location at the distal end of the lead body. For example, the lumen may extend to tip electrode 12. This side lumen 32 may be formed of PTFE such that the inner lumen is collapsible. For example, a PTFE tube may be affixed to the lead body 10 using any type of bio-compatible adhesive. The lumen expands to fit over a guide wire positioned in the venous anatomy for the purpose of directing the lead to the site of implant. When the guide wire is removed, the lumen will collapse or fold down against the lead body 10. The distal end of the lumen may be closed, or a stop member 33 may be provided at the lumen distal end to prevent a stylet advanced within the lumen from extending beyond the lumen distal end and possibly damaging tissue.

According to yet another aspect of the invention, additional collapsible PTFE lumens as may be formed of PTFE tubing may be added around the lead body. Each of these tubes will further selectively promote tissue in-growth, and, may be positioned to urge one or more of the electrodes against tissue after the implant procedure. These additional lumens may further be used during an implant procedure in conjunction with a guidewire or stylet to steer a lead around a curve within the vascular system.

In one embodiment, the distal end of the lead body is sized to be positioned within a branch vein as a means of fixation. In this embodiment, the diameter of lead body 10 may range from approximately 0.030" to 0.090", and in a more specific embodiment may range from approximately 0.040" to 0.065". In such an embodiment, all electrodes have a diameter similar to that of the lead body to allow for placement of the lead within the coronary vessels.

FIG. 2 is a posterior view of the heart illustrating the lead system of FIG. 1 implanted within a branch vein of the coronary sinus. Branch vein 60 may be any of the branch veins draining into the coronary sinus 62, including the posterior lateral vein (PLV), lateral vein, or great cardiac vein (GCV).

Positioning of the lead may be completed using several methods. During the implantation procedure, a guide catheter may be used to cannulate the ostium 64 (shown dashed) of coronary sinus 62. A guidewire may then be pre-loaded into side lumen 32, and the guidewire and lead may be delivered within the lumen of the guide catheter into the coronary sinus 62. Thereafter, the guidewire may be advanced beyond the distal tip of the lead and navigated into the selected branch vein. This process may be aided using fluoroscopy. A radiopaque marker such as marker 53 (FIG. 2) may be provided on a distal end of the guidewire and/or lead body 10 to aid in this process, for example. The guide catheter provides back up support for the navigation of the guide wire and lead during the location of the branch vein. After placement of the lead at the target location, the guidewire and guide catheter may then be removed from the body.

In another embodiment wherein the side lumen 32 includes a closed distal end, a stylet may be pre-loaded in the lumen, and the lead and stylet combination advanced within the lumen of the guide catheter to the coronary sinus 62. Thereafter, the stylet may be used to advance the lead distal end past the guide catheter distal end and into the desired branch vein. The guide catheter and stylet may then be removed from the body.

In yet another embodiment, the lead need not include a side lumen, but instead includes a lumen within the lead body, as may be defined via a coiled conductor in the manner discussed above. A stylet may be pre-loaded into this internal lumen so that the lead and stylet may be advanced into the coronary sinus in the manner discussed above, and thereafter positioned within a branch vein. According to yet another embodiment of the invention, the internal lead lumen may extend through the distal end of the lead, and a guidewire may be used to place the lead in a manner similar to that discussed above with respect to the side lumen. That is, after the guidewire and lead are positioned within the coronary sinus, the guidewire is advanced to sub-select the branch vein, and the lead is then tracked over the guidewire to the target destination. The guidewire and guide catheter are thereafter removed from the body.

As shown in FIG. 2, the distal portion of the lead may be positioned with tip electrode 12 wedged into branch vein such that the shocking electrode 16 extends proximally along the vein and with ring electrode 18 positioned near the location where the branch vein drains into the coronary sinus. Another lead 70 having a pace/sense electrode pair 72 and a defibrillation coil 74 may be implanted in the right ventricular apex. When a high-voltage shock is deliver, current flows between defibrillation coils 16 and 74 along shock path 76. By electrically coupling either the tip electrode 12 or the ring electrode 18 to the defibrillation coil during the delivery of the shock, the current path may be widened to affect more tissue, increasing efficacy of the therapy.

After the leads are positioned within the patient, they may be coupled to an implantable medical device (IMD) 80. The implanting physician may then perform electrical testing to determine whether tip electrode 12 or ring electrode 18 provides the best location for bi-ventricular pacing. Temporary contacts can be made with the connectors at the proximal end of the lead to test the most distal electrode 12 versus the most proximal electrode 18 as the cathode with the other two electrodes serving as the anode. Selection of the cathode is based on the efficiency of bi-ventricular pacing. This selection can be made by programming the pulse generator, or by providing a separate jumper connector to a pin grid array at the proximal end of the lead body 10.

As described further below, after lead implantation is completed, a physician may conduct testing to determine whether the tip electrode 12 or ring electrode 18 are associated with better pacing thresholds, and should therefore be selected as the cathode. After this determination is complete, the connection system of the current invention may be used to accomplished the selected configuration as discussed further below.

B. Connection System of the Current Invention

As shown in FIG. 1, a multi-polar lead as may be used with the current invention includes multiple conductors, each electrically coupled to a respective connection member such as a pin. The pin is provided by connector 140 at the proximal end of the lead body 10. Using the current example, shocking conductor 23 is coupled to pin 146, conductor 21 is coupled to pin 142, and conductor 25 is coupled to a third pin (not shown in FIG. 1.) FIG. 1 further illustrates a lockout member 149 to be discussed further below.

Figure 3:
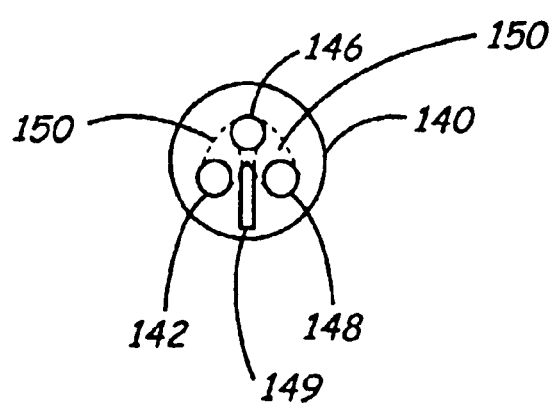
FIG. 3 is an end view of one embodiment of the connector system of the current invention.

FIG. 3 is an end view of connector 140, illustrating connection members shown as pins 142, 146, and additional pin 148, which is electrically coupled to conductor 25. This view further illustrates lockout feature 149. In this embodiment, the pins of connector 140 are equidistant from one another. These pins may be joined to a mating interface on the inventive connector system in several different orientations, as illustrated in FIG. 4.

Figure 4:
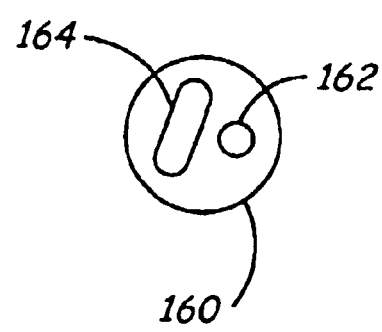
FIG. 4 is an end view illustrating a mating interface for use with the connector system of FIG. 3.

FIG. 4 is an end view of a mating interface 160 for use with connector 140 of FIG. 3. The mating interface includes a first port 164 that is oblong, and is designed to mate with, and electrically couple to the coil electrode and the selected anode. That is, port 164 will receive either pins 146 and 142, or pins 146 and 148. The two options are shown by dashed lines 150 of FIG. 3. Mating interface 160 further includes a second port 162 that is circular to receive the pin that is electrically coupled to the electrode selected to be the cathode. As discussed above, since either tip electrode 12 or ring electrode 18 will be selected as the cathode, second port 162 will be coupled to either pin 142 or 148.

Lockout member 149 may optionally be provided as a protruding ridge between pins 142 and 148 to prevent mating interface 160 from receiving the combination of pins 142 and 148, since this would select shocking electrode 16 as the pacing cathode, with the remaining two electrodes selected to deliver high-voltage shocks. In another embodiment, color-coding may be provided to indicate the various possible connection combinations that may be made to the connector 140. For example, the connection member associated with a coil electrode of a lead may be color-coded to indicate that that connection member should not be selected as the cathode connector.

Figure 5:
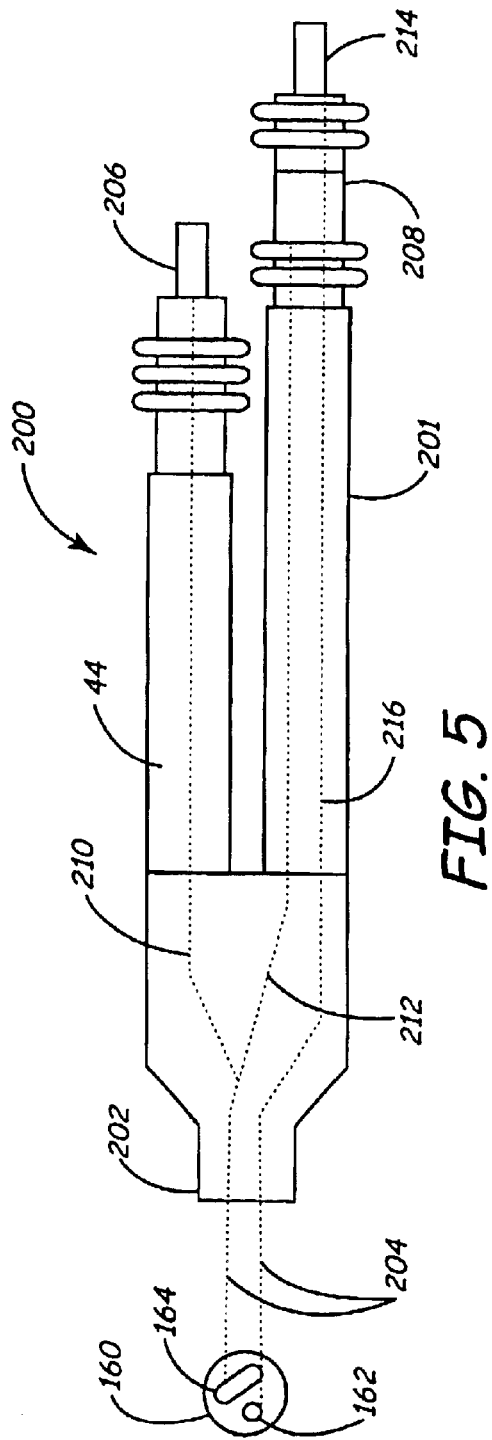
FIG. 5 is a side view illustrating use of the mating interface of FIG. 4 incorporated within a connector system that includes a standard DF-1 connector.

FIG. 5 is a side view illustrating use of mating interface 160 incorporated within an adapter that includes a bi-furcated connector sleeve 198. The connector sleeve 198 is coupled to a standard DF-1 connector 200 and a standard IS-1 connector 201 at the proximal end. Mating interface 160 is shown in cross-section to illustrate the various electrical connections associated with the adapter, although it will be appreciated that this mating interface is actually included within a distal end 202 of the adapter.

Dashed lines 204 illustrate the electrical connections associated with the ports of mating interface 160. Port 164 is electrically coupled to connector pin 206 and ring connector 208 of adapter via conductors 210 and 212, respectively. Similarly, port 162 is electrically coupled to pin connector 214 via conductor 216. By selectively coupling port 162 to either pin 142 or 148 of connector 140, then coupling pins 206 and 208 to a connector block of a pacemaker cardioversion/defibrillator as is known in the art, the desired electrical connections as determined by threshold testing may be obtained. A high-voltage shock may then be delivered via pin 206 and conductor 210, whereas pacing therapy may be delivered via pin 214, with the return current path being provided by pin connector 206 and ring connector 208.

Figure 6:
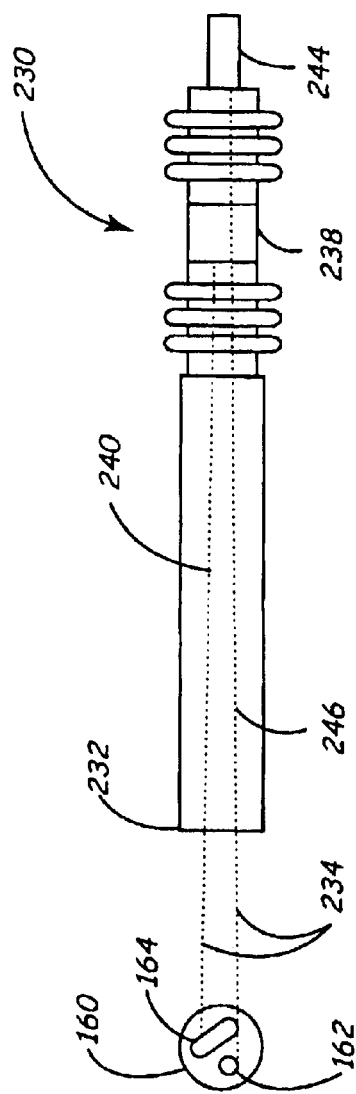
FIG. 6 is a side view illustrating use of the mating interface of FIG. 4 incorporated within a connector system that includes a standard IS-1 connector.

FIG. 6 is a side view illustrating use of mating interface 160 incorporated within an adapter that includes a standard IS-1 connector 230 at the proximal end. As with FIG. 5, mating interface 160 is shown in cross-section to clarify the electrical connections, and it will be appreciated the mating interface is actually included within the distal end 232 of adapter. Dashed lines 234 illustrate the electrical connections associated with mating interface 160. Port 164 is electrically coupled to ring connector 238 of adapter via conductor 240. Similarly, port 162 is electrically coupled to pin connector 244 via conductor 246. By selectively coupling port 162 to either pin 142 or pin 148 of connector 140, then coupling pin connector 246 and ring connector 238 to a connector block of a pacemaker as known in the art, the desired electrical connections as determined by threshold testing may be obtained. In this embodiment, pacing therapy may be delivered via pin 244, with the return current path being provided by ring connector 238. As will be appreciated, in this embodiment, shocking electrode 16 (FIG. 1) is used only as the anode for pacing therapy, and is not utilized to delivery high-voltage therapy.

Although FIGS. 5 and 6 contemplate the use of adapters that include industry-standard connectors such as IS-1 and DF-1 connections, this need not be the case, and any type of industry-standard or non-standard connector may employed within the connection system of the current invention.

Figure 7:
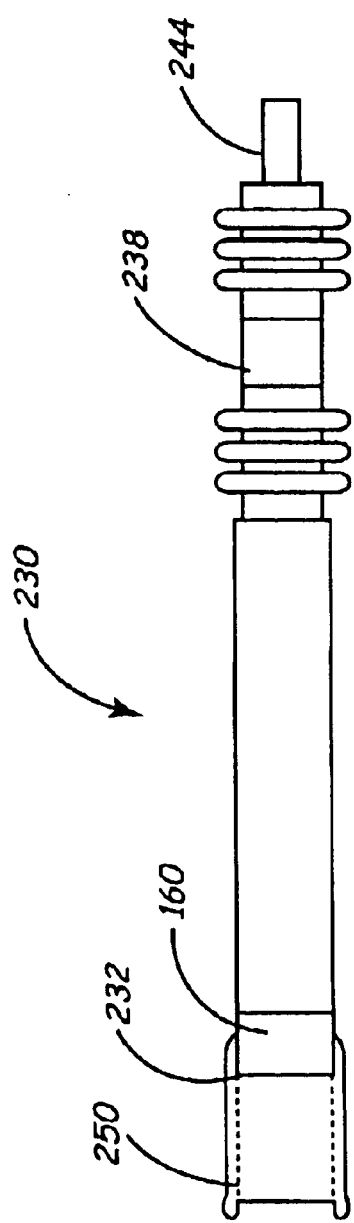
FIG. 7 illustrates the inventive connector system including a flexible roll-back sleeve.

FIG. 7 is a side view of an adapter that is similar to that shown in FIG. 6, and which further includes a roll-back sleeve 250. This sleeve may be formed of a flexible, biocompatible polymer such as silicone, and is rolled over the proximal end of a lead such as a lead shown in FIG. 1. This forms a hermetic seal that prevents fluid ingress around the connector pins of connector 140 and the ports of mating interface 160, and provides strain relief to improve structural integrity.

Figure 8:
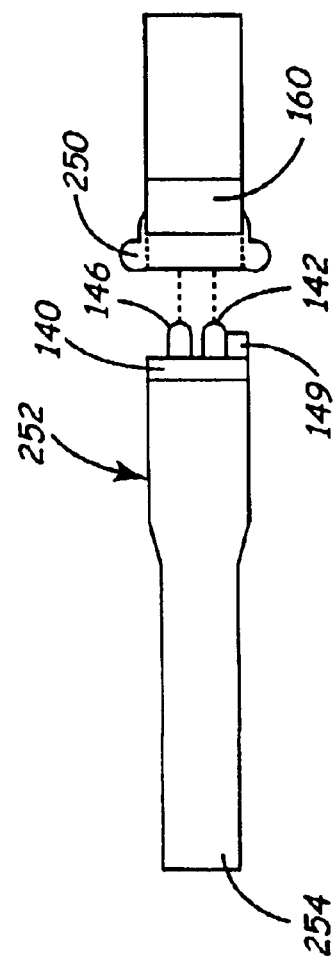
FIG. 8 illustrates the inventive connector system of FIG. 7 being coupled to a lead similar to that shown in FIG. 1.

FIG. 8 illustrates an adapter such as shown in FIG. 6 being coupled to a lead 254 of a type as shown in FIG. 1. In this view, roll-back sleeve 250 is in a folded, or "rolled-back", position to allow for easy connection between connector 140 and mating interface 160. After this connection is made, roll-back sleeve is unfolded to a position similar to that shown in FIG. 7. In this position, roll-back sleeve extends over connector 140, and further over the proximal end 252 of lead 254.

As noted above, to determine the optimal configuration for a lead according to the current invention, threshold testing or other testing may be performed. During this testing, various pins of connector 140 may be temporarily coupled. This can be accomplished using adaptors having clips similar to "alligator" clips.

Figure 9:
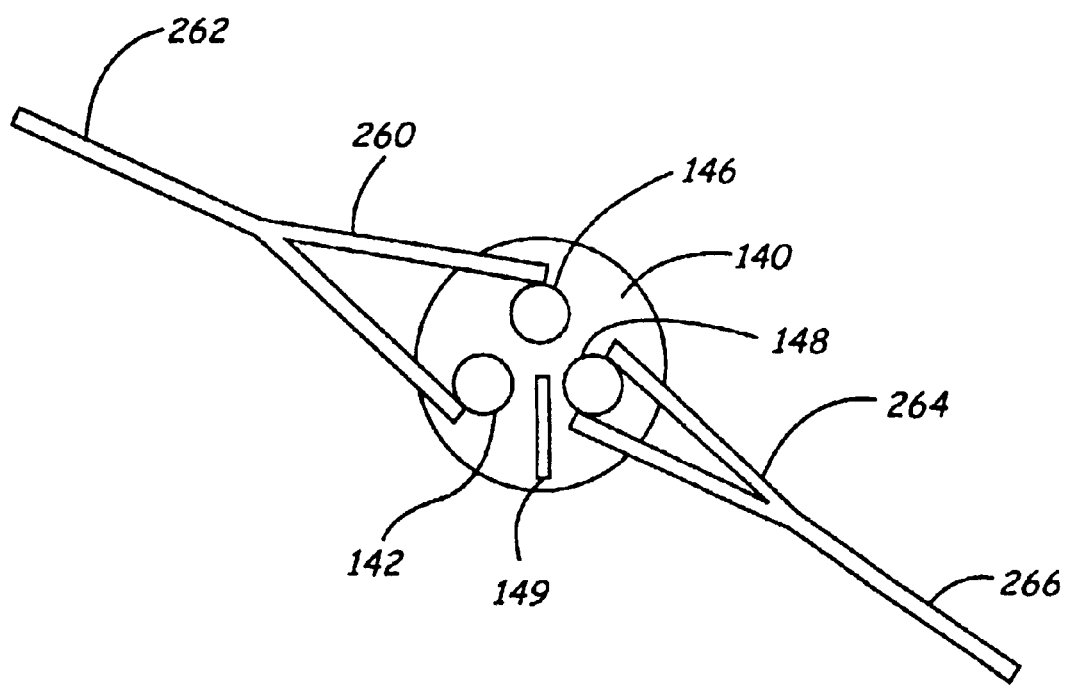
FIG. 9 is an end view of a lead similar to that shown in FIG. 1 being temporarily configured for threshold testing.

FIG. 9 is an end view of connector 140 showing temporary electrical coupling of pin 146 to pin 142 using a clip 260. Clip 260 is coupled to a distal end of lead 262. Proximal end of lead 262 (not shown) may be coupled to pulse generation equipment suitable for performing threshold testing during the implant procedure. Similarly, clip 264 is temporarily coupled to pin 148 so that proximal end of lead 266 may be coupled to pulse generation equipment for testing purposes.

One skilled in the art will recognize that many variations of the current invention connector system exist within the scope of the current invention. For example, connector 140 may include any number of connection members, or pins. Mating interface may be formed in virtually any shape as required to mate with a connector 140 at a proximal end of a lead, and the ports of mating interface may likewise be formed in a variety of shapes and sizes to accommodate the connection members of connector 140. If desired, the mating interface may include protruding connection members such as pins, whereas the connector 140 includes receptacles to receive the pins.

Figures 10A, 10C:
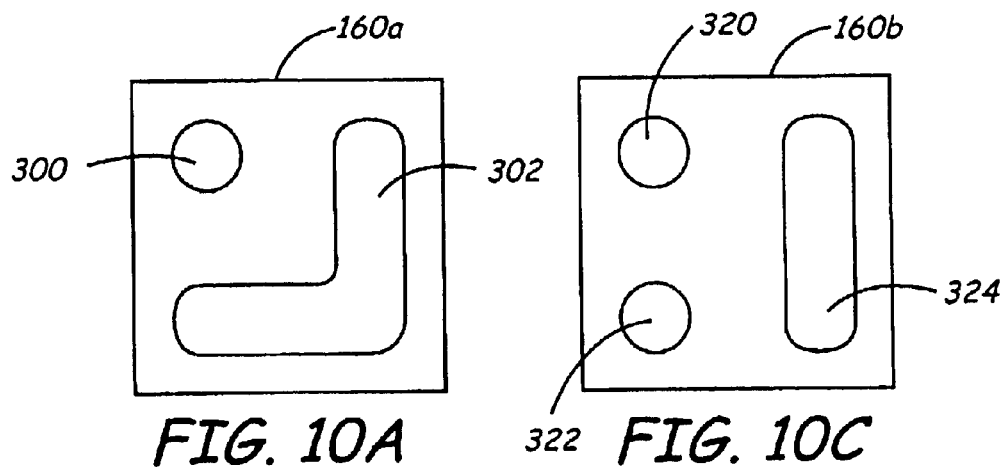

FIG. 10A is an end view of another embodiment of mating interface 160 as may be employed by the current invention. This mating interface 160*a* includes a substantially circular port 300 and a second port 302 that includes an angled channel having substantially a right-angle bend. Second port 302 is adapted to electrically couple a selected three of the connection members 304–310 of connector 140*a* of FIG. 10B, wherein connector 140*a* is a variation of connector 140 (FIG. 3).

Mating interface 160*a* may be arranged in a selected one of four positions relative to the connection members of connector 140*a*. One or more lockout members similar to lockout member 149 (FIG. 3) may be provided to prohibit certain ones of the combinations from being made. In the illustrated example, color coding is used to indicate that connection member 304 is coupled to a coil electrode and is therefore not to be coupled to port 300 of mating interface 160*a*.

The type of mating interface shown in FIG. 10A may be used to couple two pace/sense electrodes in common with a coil electrode, for example. A remaining electrode may be selected as a pace/sense cathode by electrically coupling that electrode to port 300.

FIG. 10C provides yet another variation of the mating interface 160. This mating interface 160*b* includes two substantially circular ports 320 and 322, each to couple to a respective connection member of connector 140*a*. The illustrated mating interface further includes a third port 324 to electrically couple the remaining two connection members to one another.

Figures 10B, 10D:
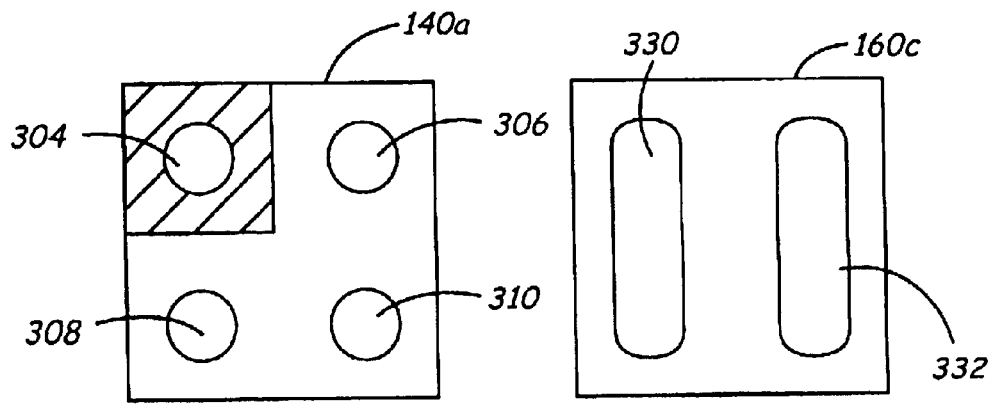
FIG. 10B is an end view of an exemplary lead connector as may be used with the mating interface of FIG. 10A.
FIG. 10D is an end view of another variation of the mating interface.

FIG. 10D is an end view of another variation of the mating interface 160. This mating interface 160*c* includes two channels 330 and 332, each to electrically couple to two of the connection members 304–310 of FIG. 10B.

According to yet another aspect of the invention, an extension member may be joined temporarily to one or more connection members of connector 140. Such an extension member provides a means to remove a delivery catheter over the lead without losing control of the lead.

The above-described invention provides an improved connector system for use in configuring electrodes of multi-polar leads. The above use of the connector system is exemplary only, and one skilled in the art will appreciate that any configurable multi-polar lead for any cardiac, neurostimulation, Transcuteous Neurological Stimulation (TENS), spinal cord stimulation (SCS), or any other bioelectrical stimulation purposes, may likewise employ the current invention. It will be appreciated that other modifications and adaptations within the scope of the invention may be contemplated by those skilled in the art. Therefore, the above discussion is to be considered exemplary in nature, and not limiting.

What is claimed is:

1. A connection system for use in coupling a multi-polar medical electrical lead to a source of electrical energy, the connection system comprising:
    a first connecting member coupled to a first conductor extending through the lead;
    a second connecting member coupled to a second conductor extending though the lead;
    a third connecting member coupled to a third conductor extending through the lead;
    a first port shaped to selectably receive and to be electrically coupled to two of the first connecting member, the second connecting member and the third connecting member;
    a second port shaped to receive and to be electrically coupled to the one of the first connecting member, the second connecting member and the third connecting member other than the two of the first connecting member, the second connecting member and the third connecting member; and
    a connector to couple the first port and the second port to the source of energy.

2. The connection system of claim 1, wherein each of the at least three conductors is electrically coupled to protruding connection members, and wherein the first port comprises a channel to receive connection members respectively associated with the at least two conductors.

3. The connection system of claim 2, wherein the second port is adapted to receive a connection member respectively associated with the other one of the at least three conductors.

4. The connection system of claim 1, wherein the connector is bifurcated.

5. The connection system of claim 1, wherein the connector includes an IS-1 industry-standard type connector.

6. The connection system of claim 1, wherein the connection includes a DF-1 industry-standard type connector.

7. The connection system of claim 1, wherein the connection system includes a body having a distal end adjacent the first and second ports, and further comprising a roll-back sleeve adjacent the distal end.

8. The connection system of claim 1, wherein the second port is adapted to electrically couple to multiple other ones of the at least three conductors.

9. The connection system of claim 1, wherein at visible indicator is provided to aid in selectably electrically coupling the first port to at least two of the at least three conductors.

10. The connection system of claim 1, and further comprising at least one lockout member to prevent the first port from being electrically coupled to a predetermined combination of the at least three conductors.

11. A connection system for use in coupling a multi-polar medical electrical lead to a source of electrical energy, the connection system comprising:
    a plurality of electrodes;
    a first connecting member coupled to a first conductor extending through the lead to a first electrode of the plurality of electrodes;
    a second connecting member coupled to a second conductor extending though the lead to a second electrode of the plurality of electrode;
    a third connecting member coupled to a third conductor extending through the lead to a third electrode of the plurality of electrodes;
    a first port shaped to selectably receive two of the first connecting member, the second connecting member and the third connecting member, and electrically couple the corresponding ones of the first conductor, the second conductor and the third conductor to one another;
    a second port shaped to receive the one of the first connecting member, the second connecting member and the third connecting member other than the two of the first connecting member, the second connecting member and the third connecting member and electrically couple to the one of the first conductor, the second conductor and the third conductor other than the corresponding ones of the first conductor, the second conductor and the third conductor; and
    a connector to couple the first port and the second port to the source of electrically energy.

12. A medical system to provide electrical stimulation to living tissue, comprising:
    a plurality of electrodes;
    a lead having a plurality of conductors, each of the plurality of conductors being coupled to a respective electrode of the plurality of electrodes;
    a first connecting member coupled to a first conductor of the plurality of conductors extending through the lead to a first electrode of the plurality of electrodes;
    a second connecting member coupled to a second conductor of the plurality of conductors extending through the lead to a second electrode of the plurality of electrodes;
    a third connecting member coupled to a third conductor of the plurality of conductors extending through the lead to a third electrode of the plurality of electrodes;
    an energy source;
    a first port shaped to receive two of the first connecting member, the second connecting member and the third connecting member, and to electrically couple the corresponding ones of the first conductor, the second conductor and the third conductor together in common;
    a second port shaped to receive the one of the first connecting member, the second connecting member and the third connecting member other than the two of the first connecting member, the second connecting member and the third connecting member and electrically couple to the one of the first conductor, the second conductor and the third conductor other than the corresponding ones of the first conductor, the second conductor and the third conductor; and
    a connector to respectively electrically couple the first and second ports to the energy source.

13. The system of claim 12, wherein the energy source is a pulse generator.

14. The system of claim 13, wherein the energy source is an implantable medical device (IMD).

15. The system of claim 14, wherein the IMD is a cardioverter/defibrillator, and wherein the first port is adapted to be electrically coupled to receive cardioversion/defibrillation pulses from the IMD.

16. The system of claim 15, wherein the IMD is a pacemaker cardioverter/defibrillator, and wherein the second port is adapted to be electrically coupled to receive relatively low-voltage stimulation energy from the IMD.

17. The system of claim 12, wherein the connector is bifurcated.

18. The system of claim 12, wherein the connector includes an IS-1 industry-standard type connector.

19. The system of claim 12, wherein the connection includes a DF-1 industry-standard type connector.

20. The system of claim 12, wherein the connection system further includes at least one additional port, each to electrically couple to at least one additional one of the at plurality of conductors.

21. A connection system for use in coupling a multi-polar medical electrical lead to a source of electrical energy, the medical electrical lead including at least three conductors, the connection system comprising:

a first port to selectably electrically couple to at least two of the at least three conductors;

a second port to electrically couple to another one of the at least three conductors; and a connector to couple to the source of energy, wherein the connection system includes a body having a distal end adjacent the first and second ports, and further comprising a roll-back sleeve adjacent the distal end.

22. A connection system for use in coupling a multi-polar medical electrical lead to a source of electrical energy, the medical electrical lead including at least three conductors, the connection system comprising:

a first port to selectably electrically couple to at least two of the at least three conductors;

a second port to electrically couple to another one of the at least three conductors;

a connector to couple to the source of energy; and at least one lockout member to prevent the first port from being electrically coupled to a predetermined combination of the at least three conductors.

* * * * *